United States Patent [19]

Rudnick

[11] Patent Number: 4,577,049
[45] Date of Patent: Mar. 18, 1986

[54] ALKYLATION OF DURENE UTILIZING HIGH BOILING CONDENSED POLYAROMATIC COMPOUNDS

[75] Inventor: Leslie R. Rudnick, Lawrenceville, N.J.

[73] Assignee: Mobil Oil Corporation, New York, N.Y.

[21] Appl. No.: 726,572

[22] Filed: Apr. 24, 1985

Related U.S. Application Data

[63] Continuation-in-part of Ser. No. 326,469, Mar. 26, 1980, abandoned.

[51] Int. Cl.[4] .............................................. C07C 4/12
[52] U.S. Cl. .................................... 585/486; 585/471; 585/475; 585/483; 585/489
[58] Field of Search ............... 585/470, 471, 475, 483, 585/486, 489

[56] References Cited

U.S. PATENT DOCUMENTS

| | | | |
|---|---|---|---|
| 2,739,991 | 3/1956 | Hervert | 585/470 |
| 3,855,328 | 12/1974 | Hedge | 585/471 |
| 4,237,329 | 12/1980 | Kamiyama et al. | 585/475 |
| 4,320,242 | 3/1982 | Onodera et al. | 585/489 |

OTHER PUBLICATIONS

Schwartz et al., *Surface Active Agents, Their Chemistry and Technology*, vol. 1, p. 113, (1949).

Primary Examiner—Curtis R. Davis
Attorney, Agent, or Firm—A. J. McKillop; M. G. Gilman; L. P. Hobbes

[57] ABSTRACT

A process is disclosed for dealkylating durene under elevated temperatures and pressures with a polynuclear aromatic compound. The dealkylation is carried out in the presence of a carbon-containing molecular sieve.

6 Claims, No Drawings

ALKYLATION OF DURENE UTILIZING HIGH BOILING CONDENSED POLYAROMATIC COMPOUNDS

This case is a continuation-in-part of U.S. patent application Ser. No. 326,469 filed Mar. 26, 1980, and now abandoned the entire contents of which are incorporated herein by reference.

This invention is concerned with the conversion of durene to more valuable products utilizing condensed polyaromatic compounds or a mixture by compounds as a receptor for transfer alkylation of durene.

It is known in the art that durene is an undesirable product in the conversion of methanol to gasoline, particularly when such reaction is catalyzed with zeolites. There are many patents and publications which describe the conversion of methanol to gasoline over zeolites, including U.S. Pat. Nos. 3,931,349; 3,969,426; 3,899,544; 3,894,104; and 3,894,102; the disclosures of which are herein incorporated by reference. As is known in the art, one particular problem residing in the conversion of methanol to gasoline over ZSM-5 type zeolites is that durene is produced in amounts higher than that expected from $C_{10}$ aromatic equilibrium distribution. Once an aromatic ring is formed in the presence of unreacted methanol, alkylation to tetramethylbenzenes occurs rapidly, but the smaller higher melting durene molecule (1,2,4,5-tetramethylbenzene, melting point 175° F.) diffuses out of the ZSM-5 pore much more rapidly than isodurene (1,2,3,5-tetramethylbenzene, or prehnite-1,2,3,4-tetramethylbenzene).

Durene is an undesirable component of gasoline because it has a high melting point and its tendency to crystallize out of solution at temperatures below 175° F. There have been various proposals advanced in order to control or minimize the amount of durene which is produced in the catalytic conversion of methanol to gasoline.

In this connection, U.S. Pat. No. 3,969,426 is concerned with a process for diminishing the amount of durene produced in a methanol to gasoline process by reacting a durene-containing stream with low boiling aromatics, such as benzene and toluene in order to transalkylate and thereby diminish the durene content. As is obvious, both benzene and toluene are very valuable products and if used to diminish durene via transalkylation reactions, it does not necessarily represent the most economically attractive method from an overall cost standpoint.

U.S. Pat. No. 4,046,827 teaches transalkylation of alkyl aromatic hydrocarbons, including durene with various transalkylating agents having an alkyl group of 1-5 carbon atoms such as toluene, xylene, trimethylbenzene, triethylbenzene, dimethylbenzene, ethylbenzene, diethylbenzene and ethyltoluene.

It has now been found that durene can be converted to $C_9$ aromatics by transfer of alkyl groups utilizing high boiling condensed polyaromatic compounds or mixtures of compounds. The polycyclic aromatic compounds useful in the novel process of this invention have boiling points on the order of at least 600° F. and are effective in lowering durene levels in the presence of catalysts such as carbon-containing molecular sieves. Polycyclic aromatic hydrocarbons having boiling points equal to or greater than 600° F. useful in the process of this invention include pyrene, fluoranthene, chrysene, phenanthrene, anthracene, fluorenes, benzphenanthrene, tetracene, coronene, pentacene, benzopyrenes, azalene, acenaphthenes, benzindanes, benzaceanthylene, cholanthrenes, perylene, picene, etc.

It is to be understood that the above compounds can be utilized either by themselves or in mixtures containing the same. Thus, for example, an FCC cycle stock having a boiling range of 600°-1075° F. was also effective in lowering durene levels due to the fact that such cycle stock contains polycyclic aromatic components.

The novel process of this invention is carried out simply by reacting durene with a polynuclear aromatic hydrocarbon such as pyrene at temperatures ranging from 700° to 900° F. and more preferably from 800° to 875° F. at elevated pressures ranging from 15 to 5000 psig and more preferably from 60 to 1500 psig. A convenient method for carrying out the novel process of this invention is to react a mixture of durene and pyrene in a sealed bomb under autogenous pressure for a period of time ranging from about 1 to 3 hours at a temperature of about 850° F.

The weight ratio of durene to the polynuclear aromatic compound is not narrowly critical and can range from 1:10 to 10:1.

As has heretofore been indicated, the novel process of this invention may be carried out in the presence of a catalyst. Preferred catalysts are carbon molecular sieves. More particularly preferred are spherical carbon molecular sieves which may have a surface area of about 1000 m²/gm and a pore size of about 13 Angstrom units. A material of this type is sold under the tradename CARBOSPHERE ® by Alltech Associates. The following examples will illustrate the novel process of this invention.

EXAMPLES 1-3

In each of Examples 1-3, 4 grams of durene and 4 grams of pyrene were placed in a sealed bomb under argon and heated at 850° F. for two hours, In Example 1, no catalyst was used. In Example 2 CARBOSPHERE ® was used.

The results are shown in the following table as expressed as relative mole percent determined by gas chromatograph/mass spectrometry:

|  | EXAMPLE | |
|---|---|---|
|  | 1 No Catalyst | 2 Carbosphere |
| Toluene |  |  |
| Xylenes |  |  |
| Trimethyl benzenes | 22.8 | 18.7 |
| Durene 36.6 | 34.5 |  |
| Iso-durene |  |  |
| Tetrahydropyrene | 1.2 | 0.8 |
| Dihydropyrene | 1.9 | 2.0 |
| Hexahydropyrene | 1.7 | 1.4 |
| Pyrene | 23.5 | 26.1 |
| Methyl pyrenes | 9.5 | 16.6 |

As can be seen from the data in Table 1, pyrene acts as an acceptor for methyl group transfer from durene to produce trimethylbenzenes. The pyrene itself has been partially converted to methyl pyrenes, dimethyl pyrenes, and hydropyrenes.

EXAMPLE 4

The process of Example 1 was repeated using 6.0 g. durene and 4.91 g. of an FCC cycle stock, under the same reaction conditions (850° F./2 hrs.) The FCC cycle stock was characterized as being highly refractory and highly aromatic.

The results obtained were as follows:

|  | FCC Cycle Stock | FCC Cycle + Durene Stock |
| --- | --- | --- |
| $C_9$ aromatics | none detected | 6.9 wt. %* |

*yield based on durene

As can be seen from the above Table, durene was converted to $C_9$ aromatics (6.9%) by the reaction of the polycyclic aromatic components in the FCC feedstock. When the FCC cycle stock was heated alone under the same conditions, no $C_9$ aromatics were observed. One additional benefit in using FCC cycle stock as a source of polynuclear aromatic compounds is that the FCC cycle stock is increased in hydrogen content by virtue of its reaction with durene due to the fact that certain components have accepted methyl groups. This results in a further increase of the value of the cycle stock, either as a hydrogen source or in further upgrading.

What is claimed is:

1. A process for the dealkylation of durene which comprises contacting durene under elevated temperatures and pressures with a polynuclear aromatic compound having a boiling point of at least 600° F., said dealkylation being carried out in the presence of a carbon molecular sieve.

2. The process of claim 1 wherein said polynuclear aromatic compound is selected from the group consisting of pyrene, fluoranthene, chrysene, phenanthrene, anthracene, fluorenes, benzphenanthrene, tetracene, coronene, pentacene, benzopyrenes, azalene, acenaphthenes, benzindanes, benzaceanthylene, cholanthrenes, perylene and picene.

3. The process of claim 1 wherein said polynuclear aromatic compound is pyrene.

4. The process of claim 1 wherein said carbon molecular sieve has a surface area of about 1000 $m_2/g$.

5. The process of claim 3 wherein said carbon molecular sieve has a pore size of about 13 Angstrom units.

6. In a method for diminishing the amount of durene produced as an undesirable product in the conversion of methanol to gasoline, the improvement which comprises contacting a durene-containing gasoline boiling range product stream produced from the conversion of methanol to gasoline with a polynuclear aromatic compound having a boiling point of at least 600° F., said contacting being carried out in the presence of a carbon molecular sieve under elevated temperatures and pressures for a period of time sufficient to convert durene to $C_9$ aromatics by transfer of alkyl groups.

* * * * *